US012766030B2

(12) United States Patent
Redar

(10) Patent No.: US 12,766,030 B2
(45) Date of Patent: Oct. 20, 2026

(54) POSITIONING DEVICE FOR THERMAL THERAPY PACKS

(71) Applicant: Genene Redar, Las Vegas, NV (US)

(72) Inventor: Genene Redar, Las Vegas, NV (US)

( * ) Notice: Subject to any disclaimer, the term of this patent is extended or adjusted under 35 U.S.C. 154(b) by 163 days.

(21) Appl. No.: 18/416,659

(22) Filed: Jan. 18, 2024

(65) Prior Publication Data

US 2025/0235346 A1 Jul. 24, 2025

(51) Int. Cl.
*A61F 7/02* (2006.01)

(52) U.S. Cl.
CPC ........ *A61F 7/02* (2013.01); *A61F 2007/0279* (2013.01)

(58) Field of Classification Search
CPC .......................... A61F 7/02; A61F 2007/0279
See application file for complete search history.

(56) References Cited

U.S. PATENT DOCUMENTS

| | | | | |
|---|---|---|---|---|
| 2012/0209363 | A1* | 8/2012 | Williams, III | A61F 7/02 607/114 |
| 2019/0322423 | A1* | 10/2019 | Baschnagel | B65D 33/30 |
| 2020/0276052 | A1* | 9/2020 | Seidenfeld | A61F 9/04 |
| 2021/0186750 | A1* | 6/2021 | Miller | A61F 7/08 |

* cited by examiner

*Primary Examiner* — Brian Handville
(74) *Attorney, Agent, or Firm* — Jason T. Daniel, Esq.; Daniel Law Offices, P.A.

(57) ABSTRACT

A positioning device for thermal therapy packs includes an elongated extension arm having a handgrip that is positioned along one end, and a frame that is positioned on the opposite end. The frame includes a plurality of walls that define a central opening and a plurality of connectors for receiving and engaging a thermal therapy device in a flat orientation. The positioning device also includes a cylindrical-shaped frame member having a plurality of connectors for receiving and securing a thermal therapy device in a rolled orientation against the outside surface of the cylindrical-shaped frame.

16 Claims, 3 Drawing Sheets

POSITIONING DEVICE FOR THERMAL THERAPY PACKS

TECHNICAL FIELD

The present invention relates generally to therapy devices, and more particularly to a positioning device for use with hot and cold temperature packs.

BACKGROUND

The statements in this section merely provide background information related to the present disclosure and may not constitute prior art.

When suffering from soft tissue injuries such as pulled muscles, sore neck, or inflammation, it is common to apply heat or cold to the affected area. As such, there are many commercially available types of hot or cold thermal therapy packs that are manufactured in a countless array of different shapes and sizes. However, regardless of the size, each of these packs are typically constructed in the same manner and include a malleable plastic pouch that contains a reusable gel or a single-use chemical agent that selectively generates sustained heat or coldness. Upon activating the pouch, the main body is positioned directly onto the skin of the affected area of the patient's body.

Although the use of thermal therapy packs is extremely common, it can be quite difficult for some users to correctly position the pack against the desired portion of their body, such as their back, feet, neck or ankles, for example. Additionally, once the pack is correctly positioned, the user must physically hold the outside of the pack against their body, thus causing their hands or fingers to be simultaneously exposed to the coolness or heat generated by the pack.

Accordingly, it would be beneficial to provide a device having a handle and an elongated arm that can allow users to position a thermal therapy pack against any portion of their body so as to overcome the drawbacks noted above.

SUMMARY OF THE INVENTION

The present invention is directed to a positioning device for thermal therapy packs. One embodiment of the present invention can include an elongated extension arm having a fixed length or a user-adjustable length. A handgrip can be positioned along one end of the extension arm for permitting a user to position the device in any number of different orientations, and a frame for engaging a thermal therapy device is positioned on the opposite end of the extension arm.

In one embodiment, the frame can include a plurality of walls that define a central opening having a shape and size that is complementary to the shape and size of a thermal therapy device in a flat orientation. A plurality of connectors can be positioned along the walls for suspending the thermal therapy device within the opening.

In one embodiment, the frame can include a generally cylindrical-shaped member having a plurality of connectors for receiving and securing a thermal therapy device in a rolled orientation against the outside surface of the cylindrical-shaped frame.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

DEFINITIONS

As described throughout this document, the term "about" "approximately" "substantially" and "generally" shall be used interchangeably to describe a feature, shape, or measurement of a component within a tolerance such as, for example, manufacturing tolerances, measurement tolerances or the like.

As described herein, the term "removably secured," and derivatives thereof shall be used to describe a situation wherein two or more objects are joined together in a non-permanent manner so as to allow the same objects to be repeatedly joined and separated.

As described throughout this document, the term "complementary shape," and "complementary dimension," shall be used to describe a shape and size of a component that is identical to, or substantially identical to the shape and size of another identified component within a tolerance such as, for example, manufacturing tolerances, measurement tolerances or the like.

As described herein, the term "connector" includes any number of different elements that work alone or together to repeatedly join two items together in a nonpermanent manner. Several nonlimiting examples of connectors include, but are not limited to, opposing strips of hook and loop material (e.g., Velcro®), attractively oriented magnetic elements or magnetic and metallic elements, thread-to-connect, twist-to-connect, and push-to-connect type devices, buckles, clamps, clips, hooks, snaps, and buttons, for example. Each illustrated connector and complementary connector can be permanently secured to the illustrated portion of the device via a permanent sealer such as glue, adhesive tape, or stitching, for example.

Figure 1:
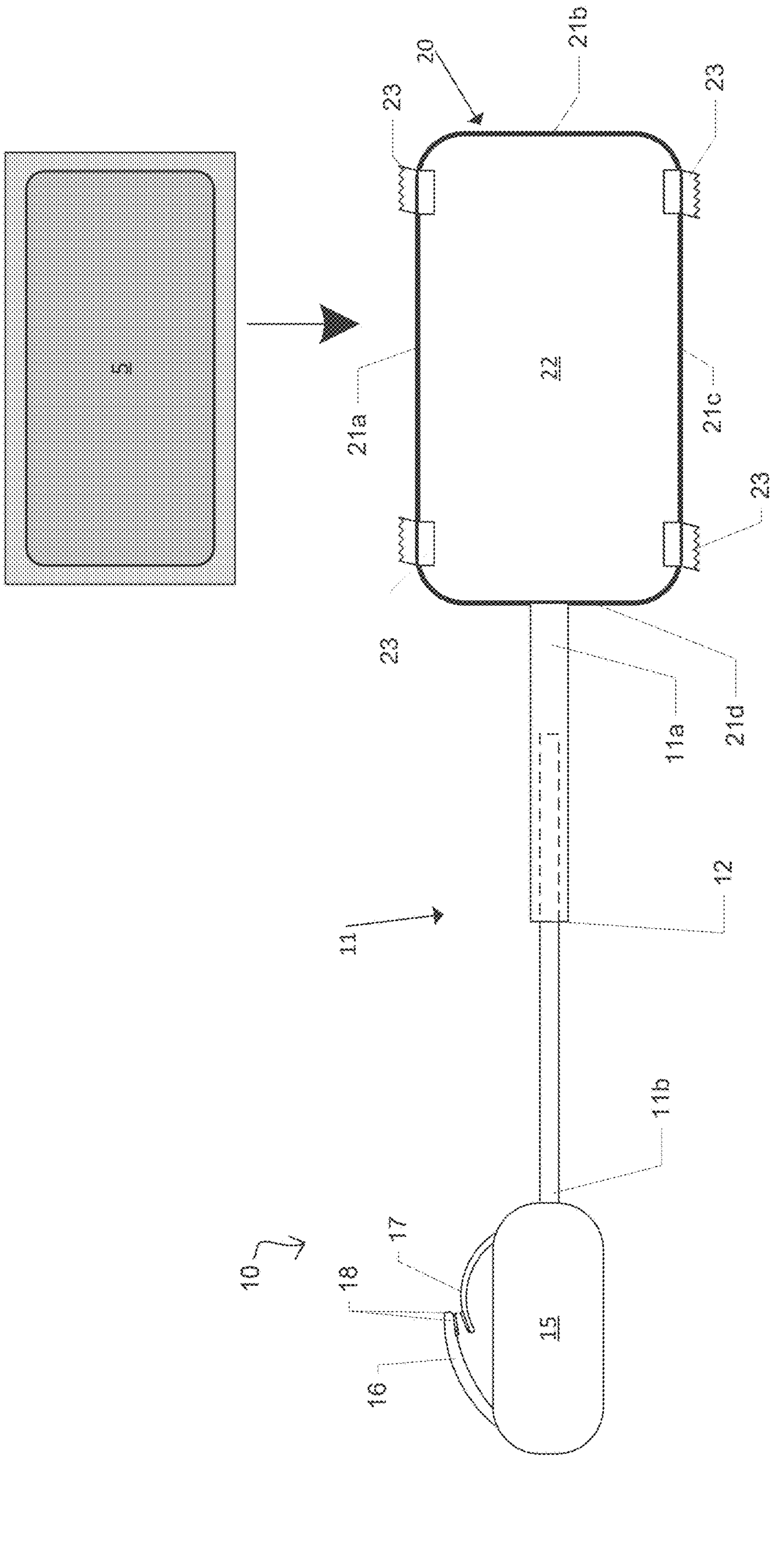
FIG. 1 is a top view of a positioning device for thermal therapy packs that is useful for understanding the inventive concepts disclosed herein.
Figure 2:
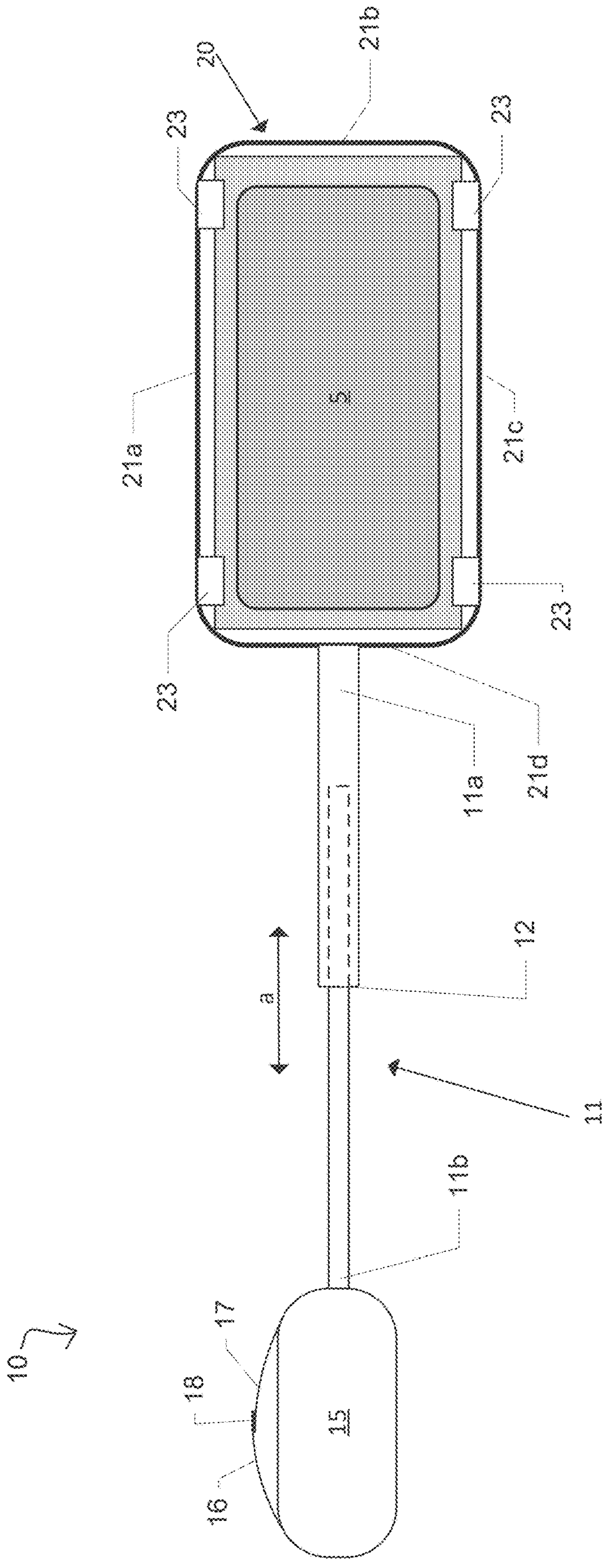
FIG. 2 is another top view of the positioning device in accordance with one embodiment of the invention.
Figure 3:
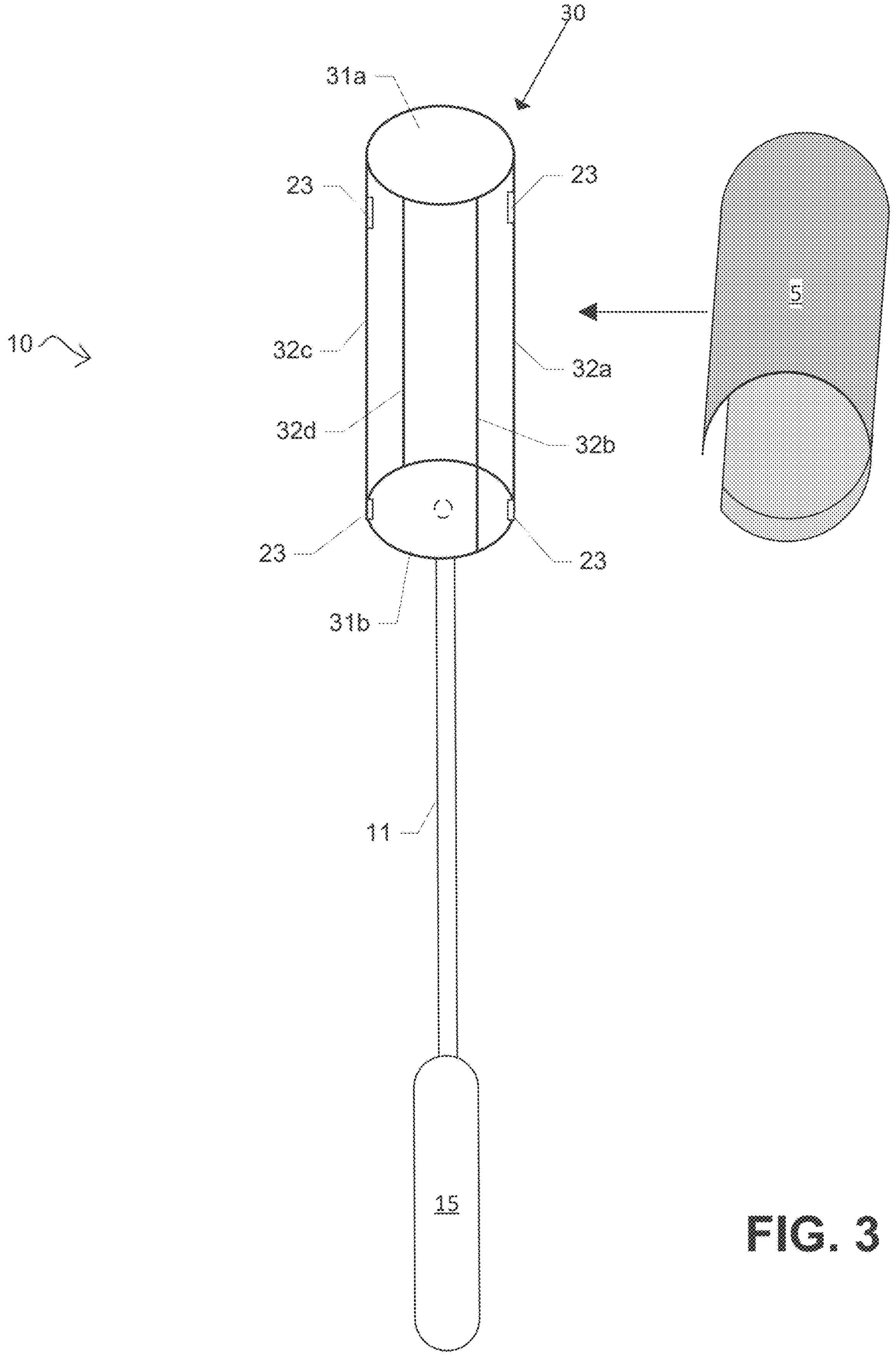
FIG. 3 is a side view of the positioning device in accordance with one embodiment of the invention.

FIGS. 1-3 illustrate one embodiment of a thermal therapy pack positioning device 10 that are useful for understanding the inventive concepts disclosed herein. In each of the drawings, identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 1.

As shown and described below, the thermal therapy positioning device 10 can include, essentially, an elongated extension arm 11 having a grip 15 along one end and a frame 20 along an opposite end. The frame can function to removably or permanently receive a thermal therapy pack, for positioning along the body by a user grasping the handle.

The extension arm 11 can function to provide physical separation between the grip 15 and the frame 20. In one embodiment, the extension arm 11 can be telescopic in nature, so as to allow the user to adjust the length of the device. To this end, the extension arm can include a fixed arm section 11*a* that is secured to the frame 20, and a sliding arm section 11*b* that extends from the grip 15. As shown, the sliding arm section can also extend from and retracts into the fixed arm section 11*a* as shown by arrow A. In one embodiment, a tensioning ring 12 can be provided along the end of the fixed arm section and can act to secure the sliding arm section at a user defined length. Of course, other embodiments are contemplated wherein the extension arm includes a fixed length (see FIG. 3) such as 12 and 16 inches, for example.

The grip 15 can function to provide a comfortable handle onto which a user may grasp and utilize the device 10. In one embodiment, the grip 15 can be constructed from a semi-malleable and high friction material such as rubber or foam, for example, so as to allow a user to securely grip the device even when their hands are moist. Of course, any number of other construction materials such as wood or plastic, for example, are also contemplated.

In one embodiment, a grip strap may be provided. As shown, the grip strap may include two strap members 16 and 17 that are positioned along each end of the grip. Each of the strap members can include connectors 18 such as opposing strips of hook and loop material, for example, to permit a user to connect the strap members together in a dimension that conforms to the user's hand. Of course, other embodiments are contemplated wherein the strap is constructed as a single element, and/or wherein the strap is located at other locations along the grip or arm section.

The frame 20 can function to receive and engage a thermal therapy pack, and can include a plurality of walls 21*a*, 21*b*, 21*c* and 21*d* which form a hollow central area 22. The frame can be manufactured to include dimensions that are complementary to any number of commercially available therapy packs 5 such as 6"×7.5" or 4.5"×10", among others, for example, and can include any number of different and/or complementary shapes such as square, oval, or round, for example.

As shown, a plurality of connectors 23 such as illustrated clamps can be positioned along the walls of the frame. Each of the clamps can transition between the open position shown at FIG. 1, and the closed position shown at FIG. 2, so as to make contact with and removably secure a thermal therapy pack 5 between the walls 21*a*-21*d*. Of course, any number of other types of connectors for removably connecting thermal therapy packs are contemplated and such connectors may be located anywhere along or within the walls of the frame body are also contemplated.

By positioning the thermal therapy pack 5 within the central opening in a flat orientation, a user can simply rotate the device to alternately position the bottom surface or the upper surface of the thermal therapy pack against the target area of their body. Such a feature is beneficial, as manufacturers recommend rotating between the top and bottom surfaces of therapy packs periodically to evenly apply the heat or coldness generated by the pack.

As noted above, the frame 20 can include any number of different shapes and sizes, as such FIG. 3 illustrates one embodiment of a circular frame 30 that includes a curved/cylindrical shape having a pair of circular ends 31*a* and 31*b* that are connected by support arms 32*a*, 32*b*, 32*c* and 32*d*. In such an embodiment, the connectors 23 can be positioned anywhere along the ends or support arms and can secure a thermal therapy pack 5 such that either the front surface or the back surface is bent around the support arms to take on the curved shape of the frame 30. Such a feature is particularly advantageous for use when applying the pack along angular portions of the body such as a user's feet, neck or shoulder area; of course the frame can be formed in any number of other shapes to which the therapy pack can be shaped and engaged to.

Although described above as including connectors for removably engaging commercially available thermal therapy packs, other embodiments are also contemplated. To this end, some embodiments contemplate the inclusion of a custom-made therapy pack that is provided as an integral component of the device 10 so as to be permanently connected onto the frame.

As described herein, the extension arm 11 and frame 20 and/or 30 may each be formed from materials that are, for example, relatively strong and stiff for their weight. Several nonlimiting examples include but are not limited to various plastic/polymers (e.g., high-density polyethylene (HDPE), rigid polyvinyl chloride (PVC), malleable polyethylene terephthalate (PET)), various natural materials (e.g., wood) and/or various composite materials (e.g., carbon fibers in a polymer matrix, fiberglass, etc.).

Additionally, one or more elements of the device 10 can be secured together utilizing any number of known attachment means such as, for example, screws, glue, compression fittings and plastic molds, among others. Although the above embodiments have been described as including separate individual elements, the inventive concepts disclosed herein are not so limiting. To this end, one of skill in the art will recognize that one or more individually identified elements may be formed together as one or more continuous elements, either through manufacturing processes, such as welding, casting, or molding, or through the use of a singular piece of material milled or machined with the aforementioned components forming identifiable sections thereof.

As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Likewise, the term "consisting" shall be used to describe only those components identified. In each instance where a device comprises certain elements, it will inherently consist of each of those identified elements as well.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A positioning device, comprising:

an extension arm having a first end and a second end;

a handgrip that is positioned along the first end of the extension arm; and a frame member that is positioned along the second end of the extension arm, said frame member including a central opening, wherein the frame member is configured to engage a thermal therapy pack and to position the thermal therapy pack within the central opening, wherein the frame member includes a plurality of walls that define the central opening, wherein the extension arm comprises an elongated straight member, wherein the first end of the extension arm extends away from the frame member, and wherein a major axis of each of the frame member and the handgrip are positioned serially with a major axis of the frame member.

2. The device of claim 1, wherein the frame walls and the central opening include a shape and a size that is complementary to a shape and a size of the thermal therapy pack.

3. The device of claim 1, further comprising:

a plurality of connectors that are disposed along the plurality of walls.

4. The device of claim 3, wherein the plurality of connectors are configured to removably engage the thermal therapy pack.

5. The device of claim 3, wherein the plurality of connectors each comprise a clamp.

6. The device of claim 1, wherein the thermal therapy pack is permanently secured within the central opening.

7. The device of claim 1, wherein each of the extension arm and the frame are manufactured as a unitary device, and the thermal therapy pack is permanently secured within the central opening.

8. The device of claim 1, wherein each of the extension arm and the frame are manufactured as a unitary device, and the thermal therapy pack is removably secured within the central opening.

9. The device of claim 1, wherein the grip is constructed from at least one of rubber or foam.

10. The device of claim 1, wherein the second end of the extension arm comprises a fixed arm section that is connected to the frame member, and the first end of the extension arm comprises a sliding arm section that extends away from the frame member.

11. The device of claim 10, wherein the sliding arm section is configured to slide within an interior space of the fixed arm section to adjust a separation distance between the grip and the frame member.

12. The device of claim 11, further comprising:

a tensioning ring that is provided along the fixed arm section, said tensioning ring functioning to selectively allow and prevent a movement of the sliding arm section relative to the fixed arm section.

13. The device of claim 1, wherein a length of the extension arm is adjustable.

14. The device of claim 1, wherein a position of the second end of the extension arm is fixed relative to the frame member, and a position of the first end of the extension arm is adjustable relative to the frame member.

15. The device of claim 1, wherein the frame member includes a flat generally rectangular shape.

16. The device of claim 1, wherein the frame member includes a round cylindrical shape.

* * * * *